United States Patent [19]

Hudson

[11] 4,131,742

[45] Dec. 26, 1978

[54] COBALT-CATALYZED OXIDATION OF HYDROCARBONS

[75] Inventor: Barry Hudson, Beverley, England

[73] Assignee: BP Chemicals Limited, London, England

[21] Appl. No.: 738,534

[22] Filed: Nov. 3, 1976

[30] Foreign Application Priority Data

Nov. 3, 1975 [GB] United Kingdom ............. 45650/75

[51] Int. Cl.$^2$ ...................... C07C 27/12; C07C 45/02; C07C 51/20; C07C 67/00
[52] U.S. Cl. ..................................... 560/241; 203/71; 203/99; 203/DIG. 11; 260/597 R; 560/248; 568/910; 562/549; 562/400; 562/504; 562/505; 562/506; 562/414
[58] Field of Search ........... 260/533 R, 533 C, 632 C, 260/597 R; 560/241; 568/910

[56] References Cited

U.S. PATENT DOCUMENTS

| | | | |
|---|---|---|---|
| 3,012,038 | 12/1961 | O'Neill et al. | ................. 260/533 R |
| 4,032,570 | 6/1977 | Schulz et al. | .................... 260/533 R |

FOREIGN PATENT DOCUMENTS 709674  6/1954 United Kingdom ................ 260/533 R

*Primary Examiner*—Vivian Garner
*Attorney, Agent, or Firm*—Brooks, Haidt, Haffner & Delahunty

[57] ABSTRACT

A process for the liquid phase oxidation of hydrocarbons with a molecular oxygen-containing gas in the presence of a dissolved cobalt salt catalyst characterized in that the oxidation is carried out in the substantial absence of chromium in the reaction medium i.e. a concentration of chromium in the liquid phase of not greater than 400 ppm.

22 Claims, 4 Drawing Figures

COBALT-CATALYZED OXIDATION OF HYDROCARBONS

The present invention relates to the cobalt-catalysed liquid phase oxidation of hydrocarbons to produce oxygen-containing organic compounds.

Processes for the liquid phase oxidation of hydrocarbons, especially saturated aliphatic hydrocarbons containing from 3 to 7 carbon atoms, in the presence of a soluble cobalt salt as catalyst to produce oxygenated reaction products including a substantial proportion of carboxylic acids are well known. However, scant attention appears to have seen paid to such oxidation processes wherein the recovered catalyst solution is recycled directly to the oxidation reaction. In the past it has been the practice to recover the cobalt catalyst from the unwanted oxidation by-products and reactor corrosion products by precipitation as an insoluble cobalt compound, followed by conversion to the soluble cobalt catalyst species. Representative of the published patent specifications describing this technique is U.S. Pat. No. 3,840,469 wherein cobalt (II) ions initially present in a first liquid medium consisting essentially of acetic acid derived from the liquid phase oxidation of an aliphatic hydrocarbon are recovered and a fresh solution of the same produced by:

(a) incorporating into said first acetic acid medium containing cobalt (II) ions and about 3 to 15 percent water by weight a source of oxalate ions in a quantity at least sufficient to react stoichiometrically with said cobalt (II) ions to form cobalt oxalate.

(b) forming a solid precipitate of cobalt (II) oxalate in said first acetic acid medium while at a temperature of about 20 to 150° C., (c) separating said precipitate of cobalt oxalate from said first acetic acid medium, (d) contacting said separated precipitate of cobalt oxalate with a second medium consisting essentially of acetic acid containing about 3 to 15 percent water by weight provided at an elevated temperature of about 60 to 140° C. and containing calcium ions dissolved therein in a quantity at least equivalent stoichiometrically to the cobalt (II) ions contained in said cobalt oxalate to form calcium oxalate, (e) forming a solid precipitate of calcium oxalate in said second acetic acid medium while said cobalt (II) ions are solubilised, and (f) separating said solid precipitate of calcium oxalate from said second acetic acid medium to produce a fresh solution of cobalt (II) ions dissolved in acetic acid.

Such a process is typical of one approach to the problem of catalyst recycle. It is involved and economically unattractive. Another approach, apparently not attempted in the past, is to examine the oxidation by-products and corrosion products with a view to eliminating or reducing to negligible proportions the formation of those components which are harmful to the oxidation reaction.

Adopting this approach we have found that chromium has a marked inhibitory effect on the oxidation reaction rate at concentrations greater than 400 ppm. Since chromium is a component of stainless steel, the material conventionally used for the fabrication of reaction vessels, corrosion inevitably leads to the presence of chromium in the liquid reaction medium in contact with stainless steel surfaces; the longer the duration of contact the greater being the concentration of chromium in the reaction medium. Consequently, we have found it impossible to maintain continuous oxidation in a stainless steel reactor with recycle of the catalyst solution over extended periods.

Thus the present invention provides a process for the production of oxygen-containing organic compounds by the oxidation of a hydrocarbon feedstock with a molecular oxygen-containing gas in the presence of from 0.1 to 10 percent by weight, based on the weight of reaction medium, of a soluble cobalt compound other than the halide as the sole catalyst, and an essentially inert reaction medium at a temperature in the range 70 to 150° C. and at a pressure sufficient to maintain the reactants in the liquid phase characterised in that the oxidation is carried out in a reaction vessel either fabricated in or lined, on at least that part of the internal surface thereof in contact with the liquid reaction medium, with a substantially chromium-free material when the cobalt catalyst is separated from the oxygenated products as a solution in the inert reaction medium and returned to the oxidation.

By substantially chromium-free material within the context of the present application is meant a material which on prolonged contact with liquid reaction medium does not lead to a concentration of chromium in that reaction medium of more than 400 ppm.

Substantially chromium-free materials which may be used include glass, resins, porcelain, enamel, titanium, tin and high nickel content alloys such as Hastelloy B. The preferred material is titanium.

The hydrocarbon to be oxidised may be a saturated aliphatic hydrocarbon, a cycloaliphatic or alkyl aromatic hydrocarbon. It is preferred to employ a saturated aliphatic hydrocarbon containing from 3 to 7 carbon atoms. An especially preferred hydrocarbon is butane. The butane is preferably used in the form of n-butane but may contain isobutane and minor amounts of other saturated hydrocarbons. Although isobutane may be present in greater proportions, it is preferred that the n-butane contain not more than 40% w/w isobutane.

The molecular oxygen-containing gas may be substantially pure oxygen or may be any gas mixture containing molecular oxygen. It is preferred to employ air, because the likelihood of forming explosive mixtures in the unreacted gas withdrawal system can be prevented far more easily than when using substantially pure oxygen or gaseous mixtures containing higher concentrations of molecular oxygen than air. Alternatively substantially pure oxygen may be introduced into the reaction mixture together with recycled (recirculated) off-gases from the oxidation process as a means of reducing the likelihood of forming explosive mixtures in the unreacted gases.

The oxidation is carried out in a liquid phase comprising the hydrocarbon to be oxidised and, in addition, an essentially inert liquid reaction medium. The latter may be any essentially inert liquid in which the cobalt compound catalyst is soluble. It is preferred that the inert reaction medium comprises a lower acid having from 2 to 4 carbon atoms such as acetic acid, propionic acid or normal butyric acids. When butane is the saturated aliphatic hydrocarbon, it is preferred to employ acetic acid since it is the desired product and separation procedures are simplified. Other inert reaction media such as benzene, chlorobenzene, phenyl benzoate or benzoic acid may be used. The amount of the inert reaction medium employed is not critical provided that sufficient is used to provide a substantially homogeneous reaction medium throughout the course of the oxidation reaction. The weight ratio of inert reaction medium to hydrocarbon may be in the range 1:10 to 100:1.

The cobalt catalyst may be any cobalt salt soluble in the reaction medium. Suitable examples include cobalt sulphate, nitrate, acetate, propionate, butyrate, isovalerate, benzoate, toluate, naphthenate, salicylate, phthalocyanine or acetyl acetonate. The cobalt catalyst may be introduced as a cobalt salt in which the cobalt is in the +2 or +3 oxidation states or partially in the +2 and +3 oxidation states. Preferred salts are cobaltous and cobaltic acetates or a mixture thereof. Even more preferably not less than 5 and not more than 90 percent of the cobalt catalyst is introduced into the reaction vessel in the +3 oxidation state in a continuous process and not less than 11 and not more than 90 percent of the cobalt catalyst is introduced into the reaction vessel in the +3 oxidation state in a batch process. Using these particular catalysts it is not necessary to employ a co-oxidant because the long induction period normally experienced using a cobalt catalyst exclusively in the +2 oxidation state is substantially eliminated. However, if desired a co-oxidant such as methyl ethyl ketone may be employed. The amount of the cobalt catalyst employed, calculated as cobalt, may be in the range 0.1 to 10% by weight and is preferably in the range from 0.2 to 5% by weight.

The reaction temperature is preferably in the range 90 to 140° C. and a reaction pressure in the range 10 to 100 bar absolute is usually found to maintain the reactants in the liquid phase. Reaction time is not critical, being dependent merely upon the extent of conversion required. Thus the reaction period may be in the range of from one minute to 20 hours, preferably from 10 minutes to 3 hours.

The process may be carried out in any suitable manner, either batchwise wherein the catalyst solution separated from the oxidation products is re-used in a further batch operation or continuously wherein the separated catalyst solution is continuously recycled to the oxidation, the latter method of operation being preferred.

The oxygenated products resulting from the oxidation of saturated aliphatic hydrocarbons comprise carboxylic acids in substantial proportions and minor proportions of ketones, esters and oxides of carbon, e.g. carbon monoxide and carbon dioxide. Thus the oxidation of butane results in a product comprising predominantly acetic acid, together with minor amounts of propionic acid and butyric acid, methyl ethyl ketone, sec-butyl acetate, ethyl acetate, methyl acetate, acetone, succinic acid, carbon monoxide, carbon dioxide and higher boiling products. Compared with other hydrocarbon oxidation routes to acetic acid, in the oxidation of butane by the process of the present invention the quantity of carbon monoxide, being less than 2% of the acetic acid made, is exceptionally low.

When the process is operated batchwise, the hydrocarbon, the inert reaction medium and cobalt catalyst, for example n-butane, acetic acid and Co(+2)/Co(+3) catalyst such as cobaltous/cobaltic acetate respectively may be placed in a closed reactor which is pressurised to the desired reaction pressure with a molecular oxygen containing gas, e.g. air. The temperature of the mixture may then be raised to the desired reaction temperature accompanied by stirring. Since oxygen is consumed in the reaction, additional molecular oxygen containing gas, e.g. air, may be introduced into the reactor. The reaction may be discontinued at any time but preferably when no further oxygen absorption occurs. The reaction mixture may be brought to atmospheric pressure, withdrawn from the reaction zone and separated into its components, the cobalt catalyst solution being recovered as a solution in the inert reaction medium.

Alternatively hydrocarbon, for example n-butane, and molecular oxygen containing gas, e.g. air may be fed continuously to such a reactor containing a cobalt catalyst e.g. Co(+2)/Co(+3) and inert reaction medium, e.g. acetic acid and the reaction products removed from the reactor, either partially or entirely, by continuously withdrawing substantially liquid-free gases from the top of the reactor, partially cooling said gases thereby providing a condensate which comprises a hydrocarbon-rich phase and an aqueous phase rich in acetic acid, separating the phases and thereafter recycling the hydrocarbon-rich phase to the reactor and separating the aqueous phase into its components. In this manner, as an additional benefit water is continuously withdrawn from the reaction because the ratio of water to acetic acid in the condensate from the reactor off-gas is higher than the corresponding ratio in the reaction mixture by virtue of the fact that the relative volatility of water to acetic acid is greater than unity. The withdrawal of the aqueous acetic acid-rich phase of the overhead condensate therefore leads to a lower standing concentration of water in the reaction mixture and results in a higher reaction rate and a reduced tendency for the reaction mixture to partition into two phases.

It is further preferred to treat the condensate resulting from partially cooling the substantially liquid-free gases withdrawn from the top of the reactor with a metal salt having a high solubility in water and acetic acid. A preferred metal salt is an alkali metal salt of a carboxylic acid. A particularly preferred metal salt is potassium acetate. It is preferred to treat the condensate with a concentrated solution of the metal salt in a suitable solvent. Suitable solvents are acetic acid, water or mixtures thereof. The salt dissolves preferentially in the aqueous phase rich in acetic acid and thereby aids phase separation and reduces the quantities of water and acetic acid in the hydrocarbon-rich phase, both of which are desirable objectives. The products may be removed from the concentrated metal salt solution in a single distillation or flash evaporation step and the salt solution recycled to the condensate treatment.

Alternatively, or in addition substantially gas-free liquid may be withdrawn from the base of the reactor and separated in a distillation column into a distillate fraction containing the bulk of the oxygenated reaction products and a base fraction comprising the inert reaction medium with the cobalt catalyst dissolved therein, which fraction is recycled to the oxidation.

The separated fraction comprising inert reaction medium with the cobalt catalyst dissolved therein may contain, in addition, minor amounts of higher boiling compounds, otherwise known as "heavy ends". Because of their higher boiling point the "heavy ends" may tend to build up in the catalyst solution recycle stream. For this reason it may be desirable to remove the "heavy ends" by cooling all or part of the catalyst solution recycle stream and subjecting it to settling and/or filtration prior to recycle to the oxidation.

When using cobalt partially in the +3 oxidation state as catalyst it is preferred to separate the catalyst solution in inert reaction medium from the oxygenated products by the process involving a low-residence time distillation column as described in co-pending application Ser. No. 706,197 filed July 16, 1976, now U.S. Pat. No. 4,086,267, and Ser. No. 755,148 filed Dec. 29, 1976.

Whether the reaction products be removed from the reactor by continuously withdrawing substantially liquid-free gases from the top of the reactor or withdrawing a substantially gas-free liquid from the base of the reactor or by a combination of both methods the crude catalyst-free product collected in the case of oxidation of butane comprises acetic acid, water, minor amounts of other carboxylic acids e.g. propionic acid and butyric acids, methyl ethyl ketone, sec-butyl acetate and trace amounts of alcohols and other volatile ketones and esters, the actual composition depending very much on the composition of the feedstock.

The crude product may be separated by feeding the product to a distillation column wherein a fraction comprising water, methyl ethyl ketone, sec-butyl acetate and minor amounts of alcohols and other volatile ketones and esters, which products, not including water, are collectively hereinafter referred to as "light ends", are taken off as an overhead fraction and condensed thereby forming a water-rich phase and a ketone/ester-rich phase, said water-rich phase being separated and returned wholly or partially to the column at a point near the top thereof and the ketone/ester rich phase being removed and passing the base product comprising acetic acid, water and carboxylic acid impurities to a second distillation column wherein water is removed overhead as an azeotrope leaving a base product comprising substantially anhydrous carboxylic acids. By passing the base product to a third distillation column acetic acid may be separated from the other higher-boiling carboxylic acids as a substantially pure product. The ketone/ester-rich phase removed from the first column may be further separated into substantially pure methyl ethyl ketone and sec-butyl acetate products is so-desired or may be recycled to the reactor, though their presence in the reactor is not necessary to initiate the oxidation reaction.

Alternatively the condensate from the first distillation column may be separated into a water-rich phase and a ketone/ester-rich phase, the water-rich phase being withdrawn and the ketone/ester-rich phase being returned at least in part to the column and a base product comprising substantially anhydrous acetic acid and minor amounts of other higher-boiling carboxylic acids passed to a second distillation column wherein substantially pure acetic acid is separated from higher-boiling carboxylic acids. Any ketone/ester-rich phase removed from the first distillation column may be separated to isolate methyl ethyl ketone and sec-butyl acetate or may be returned directly to the reactor.

The invention will now be exemplified with reference to the drawings in which.

Figure 1:
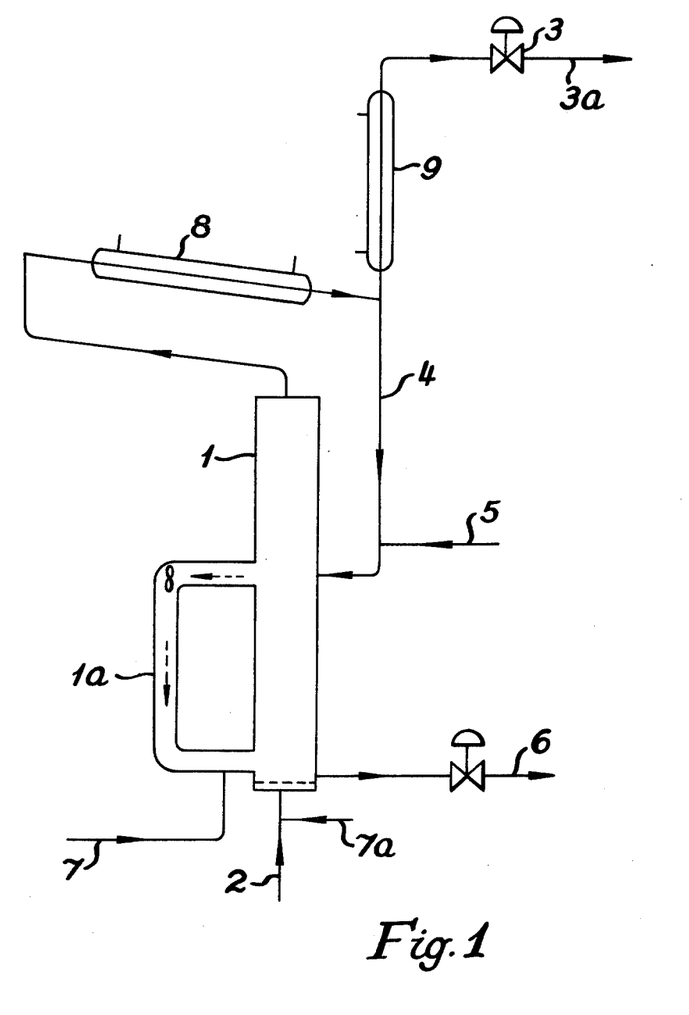
FIG. 1 is an illustration of the reactor employed for the continuous liquid phase oxidation of butane.
Figure 2:
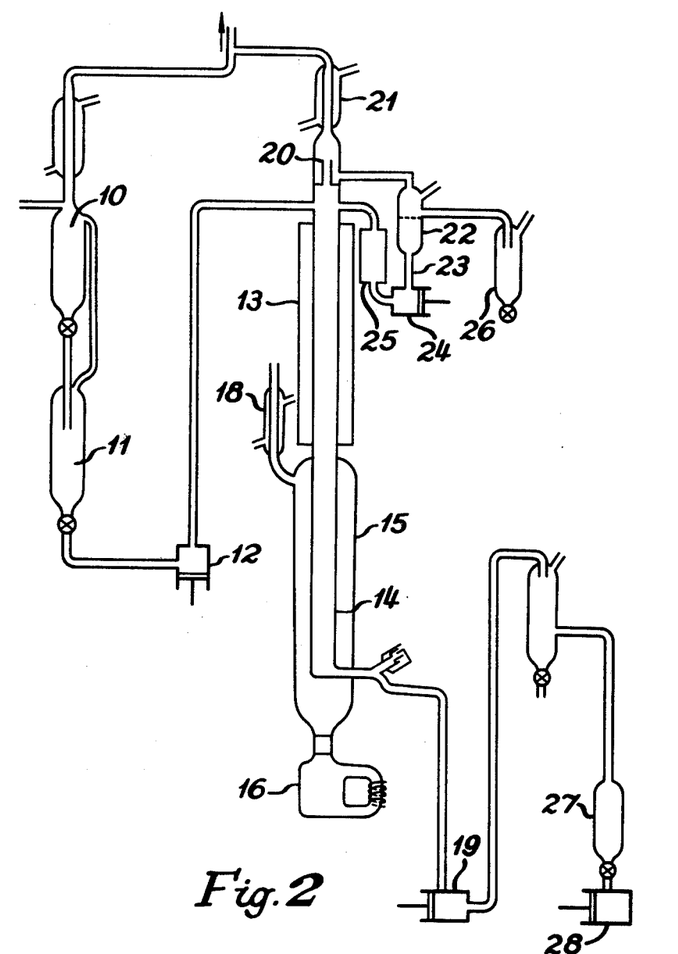
FIG. 2 is a diagrammatic representation of the distillation zone for separating the reaction products from the cobalt (+3) catalyst-containing inert reaction medium but now showing the distillation train for separating the product into its individual components.

With reference to FIG. 1 the numeral 1 denotes a reaction vessel fabricated in titanium of approximately 5 cm. internal diameter and 1 m in height having an external pipe loop 1a between the mid-point and the base; 2 is a gas inlet pipe; 3 is a reactor pressure-controlled gas release valve; 3a is a reactor off-gas line; 4 is a condensate return pipe; 5 is a butane inlet pipe; 6 is the liquid reaction mixture discharge line connecting to the distillation zone of FIG. 2; 7 is a catalyst input line; 7a is a catalyst solution recycle line; 8 is a water-cooled condenser and 9 is a refrigerated brine-cooled condenser.

With reference to FIG. 2, 10 denotes a vessel for receipt of reaction mixture from the reactor through line 6 of FIG. 1; 11 is the distillation column feed vessel; 12 is a distillation column feed pump; 13 is a thermally insulated glass column of approximately 2.5 cm inner diameter and 80 cm. in height packed with Raschig rings (6 mm) connecting through a cone and socket joint (not shown) with a falling film evaporator 14, serving as a reboiler, consisting of a glass tube of approximately 2.5 cm inner diameter and 40 cm. in height. A vapour jacket 15 surrounds the evaporator/reboiler 14, the vapor jacket being fed with propionic acid vapour from a reboiler 16 which is condensed in the condenser 18; a pump 19 controls the withdrawal of the catalyst-containing inert reaction mixture base product from evaporator/reboiler 14 which in turn controls the level of the solution within the reboiler and hence to some extent, the rate of vapour generation; 20 is a weir built into the column 13 below the level of a condenser 21; 22 is an overflow vessel from which a line 23 in the base feeds a column reflux pump 24; 25 is a reflux preheater (2-pentanol B.Pt. 119° C.); 26 is a pot for receipt of distillate from the overflow vessel 22; 27 is a catalyst feed pot and 28 a catalyst recycle pump.

Figure 3:
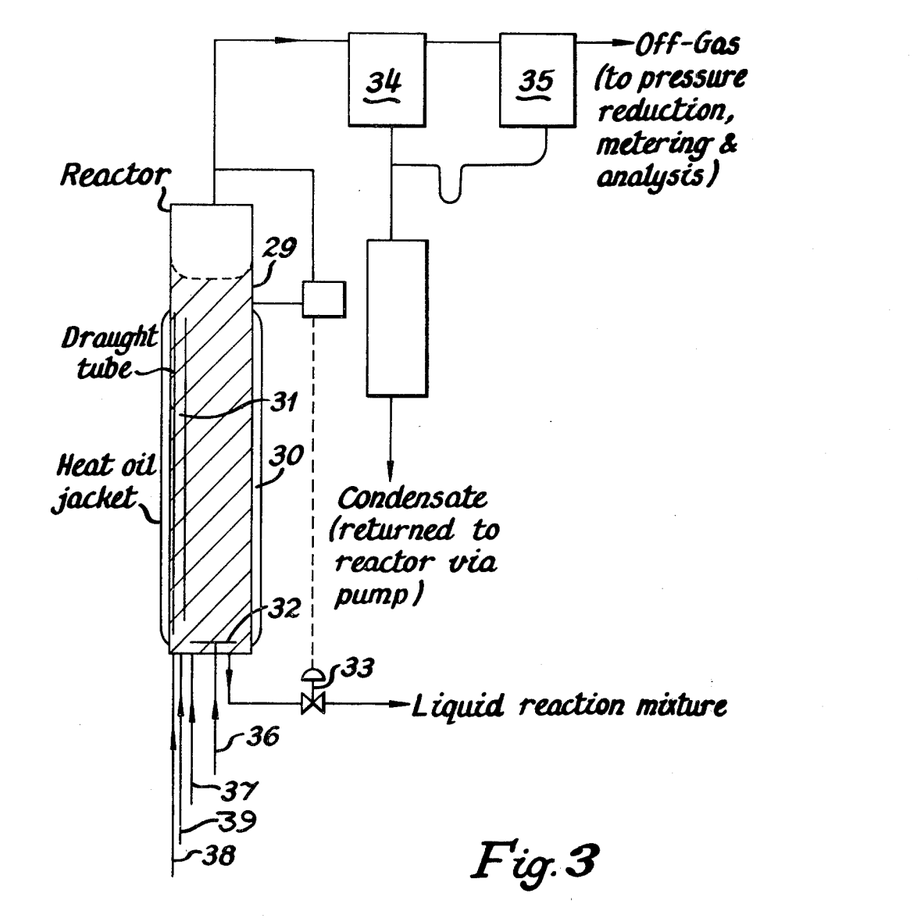
FIG. 3 illustrates a second type of reactor employed for the continuous liquid phase oxidation of butane.

With reference to FIG. 3, 29 is a reaction vessel fabricated in unstabilised 316-type (FMB) stainless steel having an internal diameter of approximately 100 mm and a height of approximately 1.5m; 30 is a heating oil jacket; 31 is a 'draught tube' of segmental cross-section, its purpose being to promote circulation of the reactor contents; 32 is an air distributor; 33 is a level-controlled liquid release valve; 35 is a water-cooled condenser; 35 is a refrigerated brine-cooled condenser; 36 is an air inlet pipe; 37 is a butane inlet pipe; 38 is a condensate return pipe and 39 is a catalyst inlet pipe also functioning as a "light ends" return pipe when operating under "light ends" recycle conditions.

EXAMPLE 1

Preparation of Catalyst Solution

Approximately 5l of acetic acid was charged to a glass vessel equipped with a gas inlet pipe and stirrer. Cobaltous acetate was dissolved in the acetic acid to provide a solution containing about 1% cobalt by weight. Oxygen at a rate of about 7l/h was passed via an OZONO (Registered Trade Mark) air conditioning unit into the stirred vessel at ambient temperature for at least 6h, thereby converting at least 80% of the cobalt acetate in the solution into the Co(+3) oxidation state. Ozone in the effluent gas was destroyed by passage through vessels containing an aqueous solution of potassium iodide.

Start-up for Continuous Operation

With reference to FIG. 1 approximately 1.3l of catalyst solution (containing about 1% w/w cobalt of which ca. 80% was in the +3 oxidation state) was introduced into the reaction vessel via line 7 and the vessel was resealed. A stream of nitrogen was introduced slowly via pipe 2 and the pressure within the reaction vessel was allowed to increase to ca. 35 bar absolute by means of the control system which regulated the gas release valve 3. About 250g butane was pumped rapidly into the reactor via pipe 5. About 350l/h, as measured at S.T.P., of air was then introduced via pipe 2 and the reactor was heated rapidly to about 110° C. by means of external electrical heating elements. Butane was introduced at about 20g/h to compensate for uncondensed butane lost in the off-gas.

By monitoring the oxygen content of the off-gases it was evident that significant oxygen absorption commenced with 15 minutes of the attainment of reaction temperature. The butane feed-rate was then increased to about 100g/h and the withdrawal of liquid reaction mixture, containing reaction products, was commenced at this time. Within 1 hour the oxygen content of the off-gases has become reasonably stable at 8 to 9% by volume.

Recovery of catalyst solution from its mixture with the organic compounds resulting from the oxidation described above With reference to FIG. 2 liquid reaction mixture was continuously withdrawn from the reactor via pipe 6 into the reactor product pot 10 held at or near atmospheric pressure, from which the greater part of the butane present in the mixture was removed as gas. The remaining liquid product (approximately 300g/h) was fed through the feed vessel 11 and the feed pump 12 to the top of column 13 where it was heated by vapours passing up the column and thereby itself separated into a vapour and liquid, the liquid passing quickly down the column into the falling-film evaporator 14 wherein both separation and passage downwards of the liquid portion were accelerated. Withdrawal of the catalyst-rich base product was controlled by the pump 19. The distillate passing up the column was condensed by the condenser 21, the condensate falling into the weir 20, from where it flowed into the overflow vessel 22, the overflow passing into the head pot 26 and the remainder being recycled through the line 23, the pump 24 and the preheater 25 to a point in column 13 approximately 10 cm. below the feedpoint, thereby providing the required level of reflux with an additional heat load on the reboiler 16.

The recovered cobalt catalyst solution in acetic acid contained approximately 0.7% by weight of cobalt of which about 40% was present in the +3 oxidation state. The solution was returned to the reactor via the catalyst feed pot 27, the recycle pump 28 and the line 7a. The residence time of the catalyst solution with the distillation zone was approximately 2 minutes.

The results presented in Table 1 indicate that the desired rate of removal of acetic acid, "light ends" and a considerable proportion of the water from the catalyst solution was effected. At the same time, a significant proportion of the cobalt was maintained in the +3 oxidation state.

TABLE 1
Short Residence Time Distillation for Separation of Oxidation Products from Catalyst Solution

|  | Feed to Distill. Zone (Reaction Mixture) | Base Product (Catalyst Solution) | Distillate (Net Reaction Products) |
|---|---|---|---|
| Feedrate (g/h) | 300 | — | — |
| Take-off rate (g/h) | — | 210 | 90 |
| Compositions (% w/w) |  |  |  |
| Water | 8.2 | 2.6 | 21 |
| Acetic Acid | 79.0 | 83.4 | 69 |
| Propionic Acid | 2.0 | 2.6 | 0.8 |
| Butyric Acid | 3.7 | 4.5 | 0.5 |
| "Light Ends"* | 2.6 | trace | 8.7 |
| "Involatils"** | 4.4 | 6.6 | — |
| Cobalt concentration (% w/w) | 0.47 | 0.7 | — |
| Proportion as Co(+3) (%) | ca. 60 | ca. 40 | — |

*Composition of the "light ends" is given in Table 2.
**Involatiles comprise compounds of cobalt, together with "heavy ends" which consist in the main of succinic acid.

Recovery of Oxidation Products with no recycle of "light ends"

The distillate from the column heads pot 26 was passed to a distillation column (not shown) of 2.5 cm inner diameter and 140 cm in height, packed with Raschig rings (6 mm) and provided with a conventional reboiler. The distillate mixture was introduced to the column near its mid-point. The fraction taken overhead from the column separated into two phases, and the whole of the lower (aqueous phase) was returned to the top of the column while the upper (ketone/ester) phase was withdrawn. The base product was withdrawn from the reboiler under liquid level control. This base product comprised all the carboxylic acids and the greater part of the water, with no ketones or esters detectable by gas-liquid chromatography. The ketone/ester phase withdrawn comprised the "light ends" of composition given in Table 2, and additionally contained about 6% water in solution.

The results obtained over a period of 48h continuous operation are given in Table 2. Continuous oxidation was maintained for a period of at least 240 hours without any significant reduction in the oxygen absorption rate.

TABLE 2

|  | Example 2 "light-ends" recycle | Example 3 "light-ends" Withdrawal |
|---|---|---|
| Reaction Temperature (° C) | 110 | 110 |
| Reaction Pressure (bar) | 35 | 35 |
| Butane Feedrate (g/h) | 105–110 | 105–110 |
| Air Feedrate (l/h S.T.P.) | ca. 350 | ca. 350 |
| Cobalt concentration in catalyst solution returned through pipe 12 (% w/w) | ca. 1.0 | ca. 0.7 |
| Porportion as Co(+3) (%) | 30 | 40 |
| Oxygen consumption (g/h) | 70 | 64 |
| Acetic Acid production (g/h) | 76 | 63 |
| Weight Selectivities (g/100g butane consumed) |  |  |
| Acetic Acid | 175 | 150 |
| Propionic Acid | 2 | <2 |
| Butyric Acid | 1 | <2 |
| "Light-ends" | — | 19 |
| "Heavy-ends" | <3 | <3 |
| Carbon Dioxide | 31 | 27 |
| Carbon monoxide | 2 | 2 |
| Composition of "light ends" withdrawn (approx. % w/w) |  |  |
| Methyl ethyl ketone |  | 70 |
| Sec-butyl acetate |  | 20 |
| Ethyl acetate |  | 5 |
| Methyl aceate |  | 2.5 |

TABLE 2-continued

| | Example 2 "light-ends" recycle | Example 3 "light-ends" Withdrawal |
|---|---|---|
| Acetone | | 1.5 |

EXAMPLE 2

Example 1 was repeated except that the "light ends" of composition given in Table 2 were recycled to the reactor 1 through the line 7a.

The results obtained over a period of about 80 hours of continuous stable operation are presented in Table 2. Continuous oxidation was maintained for a period of at least 240 hours without any significant reduction in the oxygen absorption rate.

Examples 1 and 2 illustrate that no reaction-inhibiting species (whether inorganic or organic) accumulate rapidly within the reaction/catalyst recycle system when the reactor is fabricated from titanium i.e. in a substantially chromium-free reactor.

EXAMPLE A

The reactor shown in FIG. 3, the catalyst recovery system shown in FIG. 2 and the "light ends" recovery system described in Example 1 were started-up and subsequently operated in a similar manner to the corresponding equipment in Example 1, except that all quantities and hourly feed rates were approximately 6-fold greater.

Within about 8 hours from the commencement of the experiment the oxygen absorption rate was acceptably stable at 16 ± 2 moles per hour, with recycle of both cobalt catalyst solution and "light ends", at a reaction temperature of ca. 110° C. and a total pressure of ca. 35 bar.

However, after about 20 hours of continuous operation the rate of oxygen absorption began to fall, and the butane oxidation reaction ceased within 24 hours. At the time when a significant reduction in the rate of oxygen absorption occurred the concentration of iron in the liquid reaction mixture withdrawn had risen to approximately 2000 ppm (by weight). It was only possible to restart the butane oxidation reaction after the reactor and catalyst recycle system had been drained and a fresh solution of the cobalt in acetic acid catalyst solution introduced. This behaviour was taken as an indication that a reaction-inhibiting species, probably a stainless steel corrosion product, had accumulated within the reactor/catalyst recycle system.

The approximately composition of stainless steel used in the fabrication of the reactor is presented in Table 3, together with anticipated concentrations of other metal ions which might be present in a solution containing 2000 ppm of iron, resulting from the corrosion of such a stainless steel. However, insofar as certain components of the stainless steel may be dissolved preferentially, and some components may form compounds of limited solubility, the ratios of concentrations of metals in solution may differ somewhat from those in the attacked metal.

Table 3

| Metal | Approximate Composition of Stainless Steel Reactor Used (Example A) (% by weight) | Anticipated Concentration of Metal in Solution Containing 200 ppm Iron (ppm by weight) |
|---|---|---|
| Iron | 70 | (2000) |
| Chromium | 18 | 510 |
| Nickel | 8 | 230 |
| Manganese | 2 | 60 |
| Molybdenum | 2 | 60 |

EXAMPLE B

The titanium reactor illustrated in FIG. 1 and the catalyst separation apparatus illustrated in FIG. 2 were used in the method described in Example 2 i.e. with "light ends" recycle. Under stable operating conditions an oxygen consumption rate of approximately 2 moles/hour was obtained at 110° C. and 35 bar absolute pressure to give an oxygen concentration in the off-gas of 6-8% by volume at a constant air flow rate (ca. 300 liters per hour, referred to S.T.P.). Thereafter only the oxygen concentration in the off-gas was monitored to assess the effect of introducing concentrated solutions in acetic acid of the soluble compounds of metals which are components of common stainless steels. Aliquots of the solutions were introduced into the cobalt catalyst recycle stream between the catalyst feed pot 27 and the recycle pump 28 (FIG. 2) to ensure rapid and complete transfer into the reaction vessel. The maximum concentration of added metal was estimated by assuming a feed-pipe reactor and reactor side-arm content of ca. 1.7 kg. The final distributed concentration of metal was estimated, assuming the additional contents of the liquid take-off pipe, catalyst recovery column, its (cold) feed vessel and the (cold) recycle catalyst solution holding/metering vessel to be ca. 1 kg.

Preparation of metal solutions (i) Iron
Ferric formate was dissolved in acetic acid.
(ii) Nickel
A nickel (II) - containing solution was prepared by dissolving nickel acetate in acetic acid containing a little water (ca. 10% w/w).
(iii) Manganese
A manganese (II)-containing solution was made up in the same manner as the nickel solution.
(iv) Chromium
Chromium (VI) - containing solutions were prepared by dissolving chromium trioxide in the minimum volume of water, followed by dilution of the resultant solution with acetic acid.

All solutions were freshly prepared for each test and contained at least 1% w/w metal.

Tests (a) Iron
Several aliquots of a solution containing cobalt catalyst and stainless steel corrosion products, obtained at the end of Example A, were introduced to provide a measured iron content of ca. 900 ppm, together with unmeasured amounts of other metal ions, in the withdrawn liquid reaction mixture. No adverse effect was observed. Aliquots of the concentrated solution of iron were then introduced to raise the measured iron concentration of the liquid reaction mixture to over 2000 ppm. A high iron concentration (ca 1900 to over 2000 ppm) was then maintained over a 12 hour period without any reduction of the oxygen absorption rate.

Iron concentrations were determined by dissolving the sample in an excess of an aqueous solution of ammonia and ammonium chloride. The resulting precipitate of ferric hydroxide was separated by centrifuging followed by repeated water washings and digestion with 10% hydrochloric acid. The iron present was reduced to the ferrous state by hydroxylamine and was measured colorimetrically as the 1:10-phenanthroline complex.

This method was also used to determine iron concentrations in Example A.

(b) Chromium

The introduction of approximately 1.2 g chromium in solution (to give a maximum Cr concentration of ca. 700 ppm) to the continuous reaction containing added iron led to an almost immediate cessation of oxygen absorption.

Figure 4:
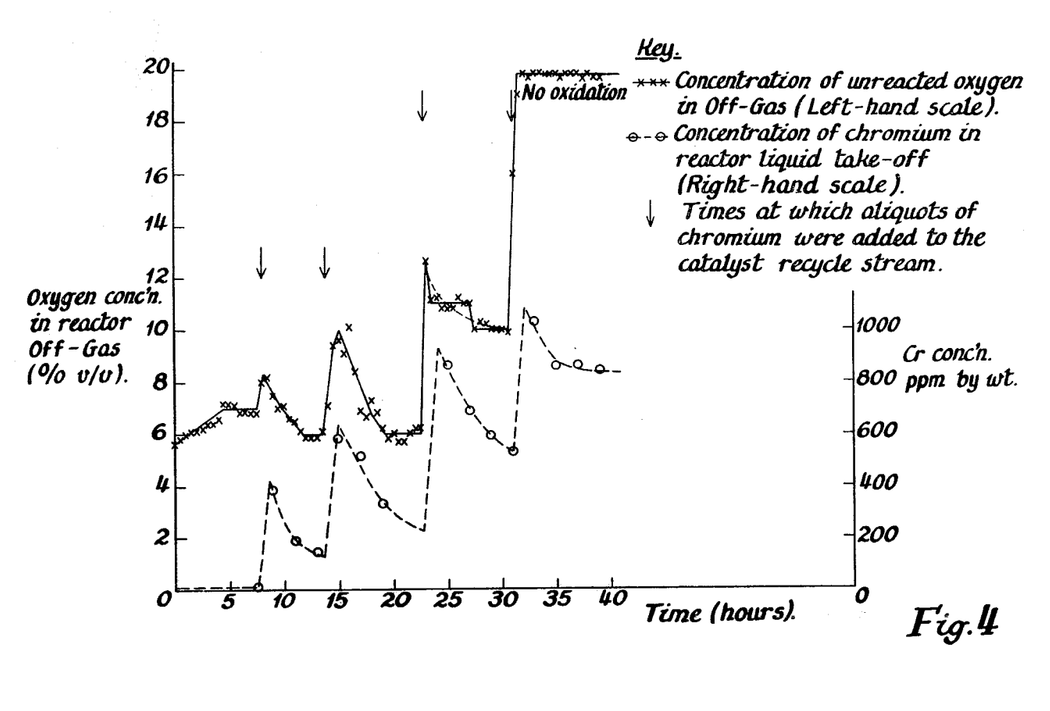
FIG. 4 is a graph showing the effect of chromium concentration on the oxygen content of the off-gas in the cobalt-catalysed oxidation of butane.

The reactor and catalyst recycle apparatus were then drained, recharged with a fresh solution of cobalt catalyst in acetic acid and butane oxidation was re-started as before. When the oxygen concentration in the off-gas was acceptably stable, aliquots of chromium (VI) - containing solution, each containing approximately 0.6g chromium, were introduced at intervals of 6 to 9 hours. The resulting changes in the oxygen concentration of the off-gas are shown in FIG. 4, together with approximate values for the concentration of chromium, as measured by Atomic Absorption Spectroscopy, in the liquid reaction mixture withdrawn.

(c) Nickel and manganese

In a similar experiment to those described in (a) and (b) above it was further demonstrated that the simultaneous presence of nickel (2.1g total) at approximately 750 ppm and manganese (1.1g total) at approximately 400 ppm did not lead to a permanent, significant reduction in the rate of oxygen absorption. Such concentrations of nickel and manganese are far in excess of those which might be present in solutions containing 400 ppm chromium resulting from the corrosion of the stainless steel used in the oxidation described in Example A.

Examples A and B are not examples according to the invention and are included for the purpose of comparison. Example A clearly shows that it is not possible to maintain a continuous reaction in a stainless steel reactor with recycle of both cobalt catalyst solution and "light ends" for a significant period of time. Example B shows that the reason for the inability to maintain a continuous reaction is the presence of chromium in the corrosion products. Examples 1 and 2 show that it is possible to maintain a continuous reaction for lengthy periods both with and without "light ends" recycle in the substantial absence of chromium.

EXAMPLE 3

With reference to FIG. 3, the stainless steel reaction vessel 29, and immediately accociated sections of piping, were replaced by essentially identical items fabricated from titanium. The titanium reaction vessel was charged with 8 liters of glacial acetic acid and was pressurized to about 35 bar (absolute). A small nitrogen flow was then established through the pipe 36. Approximately 1 kg. of butane was charged rapidly to the reactor through the line 37, and the butane feed rate was then adjusted to ca. 0.6 kg/h. The oil-heating system, 30 was switched on, and a cobalt catalyst solution, comprising 2.2% w/w cobalt, 68% as Co(+3), in acetic acid containing ca. 4% w/w water, was introduced through line 39 at a rate of ca. 1.2 l/h.

When the reactor temperature reached 60° C. air was substituted for the nitrogen stream. The oxidation reaction commenced within 15 minutes of attaining a reaction temperature of 120° C. The reaction temperature was stabilised at 125° C. and the air and butane feed rates were adjusted to provide an oxygen content in the off-gas of ca. 4% v/v and a (net) acetic acid production rate of approximately 450 g/h.

Liquid reaction mixture withdrawn from the reactor through the valve 33 was passed to a distillation column (approximately 3.5 mm in diameter and 1.8 m in height, packed with 6 mm ceramic Raschig rings), fitted with a specially designed low residence time reboiler fabricated in titanium, to provide a recovered catalyst solution containing cobalt. Recycle of this catalyst solution through line 39 commenced approximately 3 hours after start-up.

"Light ends" were separated from the reaction products in a 20-plate Oldershaw column of approximately 50 mm diameter in a manner similar to that described in Example 1. The "light ends" were thereafter recycled to the reaction vessel.

The continuous oxidation process was operated for a period of approximately 16 days with occasional interruptions, during which period no significant interruption of the oxidation reaction occured and no material was added to or withdrawn from the recycled catalyst solution, over about 7 consecutive days. During the period of operation there was no evidence of inhibition of the reaction, and reaction conditions were varied to investigate the effects of individual reaction parameters. Results obtained over 8 hours towards the end of this period are given in Table 4.

TABLE 4

|  | Example 3 "Light-ends" Recycled |  |
|---|---|---|
| Reaction Temperature (° C) |  | 130.5 |
| Reaction Pressure (bar gauge) |  | 48.3 |
| Butane Feedrate (kg/h) | ca. | 1.5 |
| Air Feedrate (m³/h at STP) | ca. | 4.6 |
| Cobalt Concentration in Reactor Product (Butane free) (% w/v) |  | 0.28 |
| Proportion as Co(+3) (%) |  | 26 |
| Cobalt Concentration in Recycled Catalyst Solution (% w/v) |  | 0.86 |
| Proportion as Co(+3) (%) |  | 10 |
| Oxygen Consumption Rate (Kg/h) |  | 1.15 |
| Acetic Acid Production Rate (kg/h) |  | 1.07 |
| Weight Selectivities (g/100 g butane consumed) |  |  |
| Acetic Acid |  | 169 |
| Propionic Acid |  | 3 |
| Butyric Acid |  | 2 |
| Carbon Dioxide |  | 39 |
| Carbon Monoxide |  | 2 |

I claim:

1. In a continuous process for the production of oxygen-containing organic compounds including a substantial proportion of acetic acid by the oxidation of a saturated aliphatic hydrocarbon containing from 3 to 7 carbon atoms or a mixture thereof in a reaction zone with a molecular oxygen-containing gas in the presence of an essentially inert reaction medium comprising a lower aliphatic carboxylic acid having from 2 to 4 carbon atoms and a soluble cobalt catalyst other than a cobalt halide in the amount, calculated as cobalt, within the range from 0.1 to 10% by weight based on the weight of the reaction medium, at a temperature in the range from 70 to 150° C. and a pressure sufficient to maintain the reactants in the liquid phase, in which a substantially gas-free liquid is withdrawn from the base of said reaction zone and separated into a fraction containing the bulk of said oxygen-containing organic compounds and a fraction consisting of said essentially inert reaction medium with said cobalt catalyst dissolved therein, said latter function being recycled to said oxidation zone, the improvement which comprises carrying out the reaction in a reaction vessel either fabricated in or lined, on at least that part of the internal surface thereof in contact with the liquid reaction medium, with a substantially chromium-free material so as to maintain the concentration of chromium in the reaction medium at a level not greater than 400 ppm.

2. A process according to claim 1 wherein said substantially chromium free material is titanium.

3. A process according to claim 1 wherein the saturated aliphatic hydrocarbon is butane.

4. A process according to claim 3 wherein the butane contains not more than 40% w/w isobutane.

5. A process according to claim 1 wherein the molecular oxygen-containing gas is air.

6. A process according to claim 1 wherein the molecular oxygen-containing gas is a mixture of pure oxygen and recycled off-gases from the oxidation process.

7. A process according to claim 1 wherein the saturated aliphatic hydrocarbon is butane and the essentially inert reaction medium is acetic acid.

8. A process according to claim 1 wherein the weight ratio of inert reaction medium to hydrocarbon is in the range 1:10 to 100:1.

9. A process according to claim 1 wherein the cobalt catalyst is cobalt sulphate, nitrate, acetate, propionate, butyrate, isovalerate, benzoate, toluate, naphthenate, salicylate, phthalocyanine or acetyl acetonate.

10. A process according to claim 1 wherein the cobalt catalyst is cobaltous or cobaltic acetate or a mixture thereof.

11. A process according to claim 1 wherein not less than 5 and not more than 90% of the cobalt catalyst is introduced into the reaction vessel in the +3 oxidation state.

12. A process according to claim 1 wherein the amount of the cobalt catalyst employed, calculated as cobalt, is in the range from 0.2 to 5% by weight.

13. A process according to claim 1 wherein the reaction temperature is in the range 90–140° C.

14. A process according to claim 1 wherein the reaction pressure is in the range 10–100 bar absolute.

15. A process according to claim 1 wherein the reaction period is in the range from 10 minutes to 3 hours.

16. A process according to claim 1 wherein part of the catalyst solution recycle stream is subjected to settling and/or filtration prior to recycle to the oxidation.

17. A process according to claim 1 wherein the cobalt catalyst has a low residence time in the distillation column.

18. A process according to claim 1 wherein the crude product fraction containing the oxygen-containing organic compounds is separated by feeding said fraction to a distillation column wherein a fraction comprising water, methyl ethyl ketone, sec-butyl acetate and minor amounts of alcohols and any volatile ketones and esters is taken off as an overhead fraction and condensed thereby forming a water-rich phase and a ketone/ester-rich phase, said water-rich phase being separated and returned wholly or partly to the column at a point near the top thereof and the ketone/ester-rich phase being removed and passing the base products comprising acetic acid, water and carboxylic acid impurities second distillation column wherein water is removed overhead as an azeotrope leaving a base product, comprising substantially anhydrous carboxylic acid.

19. A process according to claim 18 wherein acetic acid is separated from the other high-boiling carboxylic acids by passing the base product to a third distillation column.

20. A process according to claim 18 wherein the ketone/ester-rich phase removed from the first distillation column is separated to isolate methyl ethyl ketone and sec-butyl acetate.

21. A process according to claim 18 wherein the ketone/ester-rich phase removed from the first distillation column is returned directly to the reactor.

22. A process according to claim 1 wherein the crude product fraction containing the oxygen-containing organic compounds is separated by feeding said fraction to a distillation column wherein a fraction comprising water, methyl ethyl ketone, sec-butyl acetate and minor amounts of alcohols and any volatile ketones and esters is taken off as an overhead fraction and condensed, the condensate from the column is separated into a water-rich phase and a ketone-ester-rich phase, the water-rich phase being withdrawn and the ketone/ester-rich phase being returned at least in part to the column and a base product comprising substantially anhydrous acetic acid and minor amounts of other higher-boiling carboxylic acids is passed to a second distillation column wherein substantially pure acetic acid is separated from higher-boiling carboxylic acids.

* * * * *

UNITED STATES PATENT AND TRADEMARK OFFICE
CERTIFICATE OF CORRECTION

PATENT NO. : 4,131,742
DATED : December 26, 1978
INVENTOR(S) : BARRY HUDSON

It is certified that error appears in the above-identified patent and that said Letters Patent are hereby corrected as shown below:

Col. 4, line 34, after "in" and before "water" insert --both--

Col. 5, line 38, change "is" to --if--

Col. 6, line 44, "35", first occurrence, should read --34--.

Col. 13, line 9, "function" should read --fraction--

Signed and Sealed this

Second Day of October 1979

[SEAL]

Attest:

RUTH C. MASON
Attesting Officer

LUTRELLE F. PARKER
Acting Commissioner of Patents and Trademarks